(12) United States Patent
Gratwohl et al.

(10) Patent No.: US 8,016,797 B2
(45) Date of Patent: Sep. 13, 2011

(54) NEEDLE PROTECTION DEVICE WITH A BLOCKED PROTECTION POSITION

(75) Inventors: Christian Gratwohl, Aarau (CH); Marc Lanz, Lobsigen (CH); Urs Widmer, Bern (CH); Martin Wymann, Liebefeld (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 12/399,725

(22) Filed: Mar. 6, 2009

(65) Prior Publication Data

US 2009/0259196 A1    Oct. 15, 2009

Related U.S. Application Data

(63) Continuation of application No. PCT/CH2007/000438, filed on Sep. 5, 2007.

(30) Foreign Application Priority Data

Sep. 6, 2006  (DE) ..................... 20 2006 014 719 U
Sep. 6, 2006  (DE) ..................... 20 2006 014 720 U
Nov. 10, 2006 (DE) ........................ 10 2006 053 055

(51) Int. Cl.
  *A61M 5/32* (2006.01)
  *A61M 5/00* (2006.01)
(52) U.S. Cl. ......... 604/192; 604/198; 604/163; 604/171
(58) Field of Classification Search .......... 604/192–198, 604/110, 263, 241; 600/576
See application file for complete search history.

(56) References Cited

U.S. PATENT DOCUMENTS

| 4,664,654  | A  | * | 5/1987  | Strauss ......................... 604/198 |
| 4,894,055  | A  | * | 1/1990  | Sudnak ......................... 604/198 |
| 5,030,209  | A  | * | 7/1991  | Wanderer et al. ............. 604/198 |
| 6,773,415  | B2 |   | 8/2004  | Heiniger |
| 7,077,828  | B2 | * | 7/2006  | Kuhr et al. .................... 604/207 |
| 7,521,022  | B2 | * | 4/2009  | Konrad ......................... 422/103 |
| 2001/0056263 | A1 | * | 12/2001 | Alchas et al. ................. 604/193 |
| 2003/0014018 | A1 |   | 1/2003  | Giambattista et al. |
| 2003/0120209 | A1 | * | 6/2003  | Jensen et al. .................. 604/110 |
| 2005/0277893 | A1 |   | 12/2005 | Liversidge |

FOREIGN PATENT DOCUMENTS

EP    1557191 A2    7/2005
WO    01/91837 A1   12/2001

* cited by examiner

*Primary Examiner* — Kevin C Sirmons
*Assistant Examiner* — Bradley G Thomas, Jr.
(74) *Attorney, Agent, or Firm* — Dorsey & Whitney LLP; David E. Bruhn, Esq.

(57) ABSTRACT

A needle protection device for use with an injection device, the needle protection device including a moveable needle protection element which moves through a release course of movement into a locking engagement position as a result of an elastic force, the locking engagement position being achieved when the needle protection element moves from a starting position to a triggering position, when the needle protection element moves over a small portion of the release course, and being maintained when the needle protection element is no longer subjected to an external force in the triggering position.

17 Claims, 9 Drawing Sheets

NEEDLE PROTECTION DEVICE WITH A BLOCKED PROTECTION POSITION

CROSS-REFERENCED RELATED APPLICATIONS

This application is a continuation of International Patent Application No. PCT/CH2007/000438 filed Sep. 5, 2007, which claims priority to German Patent Application No. DE 20 2006 014 719.5, filed Sep. 6, 2006, German Patent Application No. DE 20 2006 014 720.9, filed Sep. 6, 2006, and German Patent Application No. DE 10 2006 053 055.1, filed Nov. 10, 2006, the entire contents of each of which are incorporated herein by reference.

BACKGROUND

The present invention relates to devices for injecting, delivering, infusing, dispensing or administering a substance, and to methods of making and using such devices. More particularly, it relates to a needle guard device which is or can be attached to an injection device of a type which may be used for administering or self-administering medicaments, for example insulin. The injection device may be a simple syringe or a syringe which is disposed of once it has been used. In such applications, the needle guard may be manufactured separately from the injection device and connected to the injection device in readiness for administering, or it may be an integrated part of the injection device and be disposed of with it. The injection device may be designed for repeated use and to enable a dose to be set or selected for the product to be administered. In some embodiments, the injection device may be an injection pen of the type used to treat diabetes and, these days, for other treatments as well.

When handling injection devices, there is a risk that patients or medical staff could be injured by an injection needle and/or be infected by an accidental stick by an injection needle that has already been used. With a view to preventing this, needle guard devices with a displaceable needle guard have been developed. For the injection, the injection device fitted with the needle guard device is pushed against the skin via the needle guard. Due to the pressure, the injection device, with the injection needle projecting from it in the distal (forward, front or injection) direction, moves in the distal direction relative to the needle guard so that the injection needle pierces the skin. Accordingly, the needle guard effects a movement in the proximal direction (rearwardly) relative to the injection device as far as a releasing position in which the injection needle projects in the distal direction beyond the needle guard by its injection portion which pierces the skin. When the injection needle is pulled back out of the skin, the needle guard is subjected to an elastic force of a rebounding element and moves in the distal direction again as far as a guard position in which it extends beyond the injection needle, including the needle tip. On reaching the guard position, the needle guard locks automatically so that it can not move back in the proximal direction relative to the injection needle again.

Such needle guard devices are known from U.S. Pat. No. 6,773,415 B2 and WO 01/91837 A1. At the end of its retracting movement, the needle guard moves into an irreversible lock, as a result of which the needle guard is no longer able to move in the distal direction into the initial position and can only move into the guard position when left to its own devices, i.e. when relived of the external force.

SUMMARY

One object of the present invention is to provide a needle guard which is easy to manufacture and which reliably protects the user against contact with the injection needle after an injection.

In one embodiment, the present invention comprises a needle guard (which also may be referred to and thought of as a needle cover or needle protector) for use with an injection device, wherein the needle guard has a needle covering position in which it can be locked. In some embodiments, the locking occurs automatically during an injection sequence, and in some embodiments, the locking is irreversible.

In one embodiment, the present invention comprises a needle protection device (which also may be referred to as a needle guard) for use with an injection device, the needle protection device comprising a moveable needle protection element (which also may be referred to as a needle cover) which moves through a release course of movement into a locking engagement position as a result of an elastic force, the locking engagement position being achieved when the needle protection element moves from a starting position to a triggering position and when the needle protection element moves over a small portion of the release course, and being maintained when the needle protection element is no longer subjected to an external force in the triggering position.

In some embodiments, the present invention comprises a needle guard device which is attached to or is designed to be attached to an injection device and has a needle holder for attachment purposes with an injection needle projecting in a distal direction. The needle guard device has a lock mechanism, which projects out from the needle holder, likewise in the distal direction, and is spaced radially apart from the injection needle, in other words radially apart from the axis extending from the distal to the proximal end. The lock mechanism comprises a hollow profile, which circumferentially surrounds the injection needle about a longitudinal portion. Also part of the needle guard device is a needle guard, which can be moved radially in the proximal direction between the injection needle and lock mechanism as far as a releasing position which releases the injection needle, and in the distal direction out of the releasing position as far as a guard position, in which it surrounds the injection needle, including the needle tip. The lock mechanism and the needle guard co-operate in a manner which ensures that the needle guard can be locked in the guard position to prevent it from moving in the proximal direction again, i.e. on reaching the guard position it is locked there. The needle guard surrounds the injection needle, thereby reliably preventing access to the injection needle in the guard position. In some embodiments, the needle guard is in the form of a circumferentially extending closed sleeve. In principle, however, it may comprises an opening or openings or orifices, provided it fulfils its guard function in the guard position, i.e. protects the user against injury due to piercing.

In accordance with some embodiments of the present invention, the needle guard is of an "early-triggering" design. This means that the lock mechanism does not lock the needle guard in the guard position until the needle guard has first reached the releasing position in which the injection needle extends beyond the needle guard by its full injection length, but also in situation where the needle guard has traveled only a smaller part of its releasing stroke out of the initial position into the releasing position and has been left to its own devices, i.e. is relieved of the external force acting in the direction toward the releasing position. It merely has to be moved into a triggering position disposed between the initial position and the releasing position to ensure that it can not move back into the unlocked initial position again once relieved of pressure. Due to the early triggering system, contamination by soiled injection needles is also prevented in situations in which the needle guard has not moved fully into the releasing position during an injection or the injection needle was extracted by only a part of its needle length corresponding to the releasing position of the needle guard for other reasons, for example if it has been handled carelessly.

In some preferred embodiments, the triggering position is selected so that the needle guard has traveled at most half of its releasing stroke when it reaches the triggering position. In some preferred embodiments, the triggering position lies at a distance corresponding to at most one third of the releasing stroke from the initial position of the needle guard. In other preferred embodiments, the stroke which the needle guard effects from the initial position into the triggering position is so short that the tip of the injection needle does not yet project beyond the needle guard when the needle guard assumes its triggering position.

In some embodiments, the needle guard may move into engagement with the lock mechanism directly, e.g. in a guiding contact, which prevents the needle guard from being able to move back into the unlocked initial position having reached the triggering position but moves into the locking connection and thus assumes its guard position. For example, one of the needle guard or lock mechanism may constitute a locating element and the other a cam guide which guides the locating element into a guiding contact when the needle guard moves out of the initial position into the releasing position. The guide has a continuous main branch, along which the locating element is guided until the needle guard has reached the releasing position, and a sub-branch branching off from it into which the needle guard moves during the movement back in the distal direction once it has reached at least the triggering position beforehand, i.e. the sub-branch branches off from the main branch at the triggering position.

In some preferred embodiments, the needle guard device also has a locking member, which is able to move relative to at least one of the needle holder or lock mechanism, to enable the needle guard to move into the releasing position on the one hand but also to prevent a movement back into the initial position if the needle guard has already reached the triggering position beforehand. The locking member is able to move relative to the needle holder or the lock mechanism, in some embodiments relative to the needle holder and the lock mechanism, from a first position into a second position. It assumes the first position whenever the needle guard is disposed in its initial position. The locking member assumes the second position when the needle guard has arrived at the triggering position from the initial position. In one preferred embodiment, the locking member prevents a movement of the needle guard into the guard position as long as the needle guard has not been moved out of its initial position into the triggering position. In the second position, on the other hand, it permits the movement into the lock connection in such embodiments, i.e. into the guard position. In another preferred embodiment, it prevents the lock connection of the needle guard from being released in the guard position, either directly or at least in a co-operating arrangement, as a result of which the needle guard can be moved out of the guard position back in the direction toward the releasing position. It is also possible for the locking member to fulfil both said functions in the second position, in other words to permit the movement into the guard position, which movement may take place relative to the locking member, and to participate in the lock connection itself.

In one embodiment, the needle guard has a locating element and the locking member has a complementary locating element, and the locating element establishes an abutting contact with the complementary locating element in the distal direction when the needle guard is in the initial position. In the direction extending transversely to the longitudinal direction of the injection needle, the locking member also has a passage extending in the longitudinal direction of the injection needle in addition to the complementary locating element. Alternatively, the passage may be provided on the needle guard in addition to the locating element. The needle guard is coupled with the locking member so that the movement of the needle guard into the triggering position causes a relative movement between the needle guard and locking member in the transverse direction. Due to this transverse movement, the locating element and the complementary locating element move out of their overlapping position and thus out of abutting contact and one of these elements moves into a position overlapping the passage. In some embodiments, the passage is provided on the locking member so that the locating element of the needle guard moves into a position axially overlapping the passage, and the needle guard is then able to move into its guard position. Depending on whether the passage is provided on the needle guard or, in some embodiments, on the locking member, a separating element extending in the proximal direction between the passage and the locating element or complementary locating element may be provided, for example integrally moulded with the locking member or needle guard. The length of the separating element as measured in the longitudinal direction corresponds to the stroke which the needle guard travels during the movement from the initial position into the triggering position. The axial length of the separating element therefore defines the length of the stroke into the initial position. During this stroke, the separating element—in engagement with the locating element of the needle guard—prevents said relative movement in the transverse direction before the triggering position has been reached.

In one development of the present invention, the needle guard device has a cam guide for the locking member. The cam guide comprises at least one guide which is inclined relative to the longitudinal direction of the injection needle and at least one locating element which is guided in a guide contact along the guide. The inclination is selected so that no friction can occur. In some preferred embodiments, it is at most 70°, measured as the angle subtended by the longitudinal axis and the guide or a parallel projection of the guide onto the longitudinal axis. One of the guide or locating element is stationary relative to the locking member and the other is stationary relative to at least one of the needle holder or lock mechanism. One of them, e.g. the locating element, may therefore be disposed directly on the locking member, for example integrally moulded with it, whilst the other, e.g. the guide, may be disposed on the needle holder, e.g. integrally moulded with it. The needle guard is coupled with the locking member so that it exerts a force on the locking member during its movement into the triggering position, which causes the locking member to move into the second position when the locating element and guide are in the guide contact.

In embodiments comprising a cam guide, the locking member is mounted so that it can rotate about the injection needle. The movement of the locking member out of the first into the second position is a superimposed translating and rotating movement along the injection needle and about the injection needle.

In some embodiments, the needle guard is advantageously coupled with the locking member via the spring element so that the needle guard expends a force via the spring element acting in the proximal direction on the locking member during the movement into the triggering position, thereby moving the latter out of the first into the second position. The spring element is biased between the needle guard and the locking member or tenses at least as the needle guard moves in the direction toward the releasing position. In some preferred embodiments, the spring element is supported directly on the needle guard and the locking member.

In the second embodiment, the locking member is able to move relative to the injection needle and lock mechanism from a proximal position, namely the first position in which it assumes an initial state, in the distal direction into the second position. The movement in the distal direction is caused by the needle guard as it moves into the guard position having reached the triggering position. The needle guard drives the locking member with it into the guard position. To achieve this driving action, the needle guard has a locating element and the locking member has a complementary locating element which move into a driving engagement with one another when the needle guard is moved in the proximal direction into or beyond the triggering position. The driving connection is a catch connection in which the locating element locates to the rear of the complementary locating element by reference to the distal direction.

Although providing the locking member means having to use an extra element, it nevertheless enables the shape of the needle guard or lock mechanism on the one hand, and that of the needle holder on the other hand, to be simplified. Due to the radially nested arrangement, the molded elements needed for locking the needle guard and establishing the driving connection can be easily produced. If the locking member is disposed radially between the needle guard and the injection needle, additional stiffness can be imparted in the radial direction.

The locking member may guide the needle guard in a sliding contact during the movement in the proximal direction. The lock mechanism and the locking member form an annular gap between them, in which the needle guard can be guided in a sliding contact on both an internal surface and an external surface respectively. A mechanical return spring is also advantageously provided for the needle guard in such an annular gap, and the annular gap thus may also axially guides the return spring. Alternatively, an annular gap may also be provided in the form of a gas-tight annular chamber, the volume of which is reduced or increased due to the movement of the needle guard to generate the elastic force for returning the needle guard in the distal direction by generating an over pressure or negative pressure.

In the second embodiment, the locating element of the needle guard not only serves as a means of driving the locking member but, in a dual function, also blocks or locks the needle guard in the guard position. In such embodiments, when the needle guard is in the guard position, the locating element moves into contact with a lock stop of the lock mechanism in the proximal direction, i.e. a movement of the needle guard in the proximal direction is prevented by the abutting contact of the locating element. To obtain such a lock in the guard position, a radial stiffening of the needle guard by the locking member is advantageous because the locking member affords radial support for the locating element to block or prevent a movement of the locating element radially inwardly in the guard position, i.e. toward the injection needle. As a result, the locating element cannot be inadvertently or deliberately be moved out of the locking engagement with the lock stop.

As the needle guard is moved into the triggering position, the locating element is moved, e.g. radially outwardly opposing a rebounding or resisting elastic force, and is moved into the driving connection by the elastic force. In the driving connection, it assumes a position which is radially farther outward than the position which it assumed in the initial state prior to the injection. The two positions are such that the locating element of the embodiments, in which it causes the needle guard to be locked in the guard position, is able to move past said lock stop of the lock mechanism in the driving connection after the needle guard has moved into the guard position but is still moved reliably in the axial direction into contact with the lock stop of the lock mechanism.

The lock stop of the lock mechanism can be moved radially outward against a rebounding elastic force, e.g. in the second embodiment. For example, the lock stop may be an elastically flexible lug. It is of advantage if the lug of the lock mechanism projects in the distal direction and accordingly has a free distal end. The free distal end constitutes the lock stop.

In some preferred embodiments, a stiff lock stop is provided on the first embodiments of the needle guard device. A stiff, non-flexible stop lock is reliable in preventing the lock engagement of the needle guard and lock mechanism from being released by manipulations and the needle guard from being able to be moved out of the guard position. A stiff lock stop can be obtained if the lock stop does not co-operate with the locating element of the needle guard but instead, in addition to the locating element, at least one lock element for the lock engagement is provided on the needle guard, as may be preferred in the case of variants of the first embodiment. The lock element may be an elastic snapper. The lock mechanism encases the lock element in the lock engagement.

In the second embodiment, the locking member forms a guide for the locating element of the needle guard. As the needle guard moves in the proximal direction, i.e. in the direction toward the releasing position, the locating element is moved radially outward along the guide against a rebounding elastic force until it snaps into the driving connection on reaching the triggering position. The guide has an inclination with respect to the proximal-distal axis as viewed across its axial extension. The inclination should be continuously, i.e. constantly, differentiable. For example, it may be constant or may decrease in the proximal direction or increase in the proximal direction, in some preferred embodiments, the biggest increase being in the second proximal half or in the last proximal third of its extension. If the locating element is shaped so that it constitutes an elastically flexible lug, this lug should project in the proximal direction, in which case it has a free proximal end.

Additional preferred features of early-triggering needle guard devices are also disclosed in German patent application No. 102006041128, which is included herein by reference.

DETAILED DESCRIPTION

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figures 1, 2, 3:
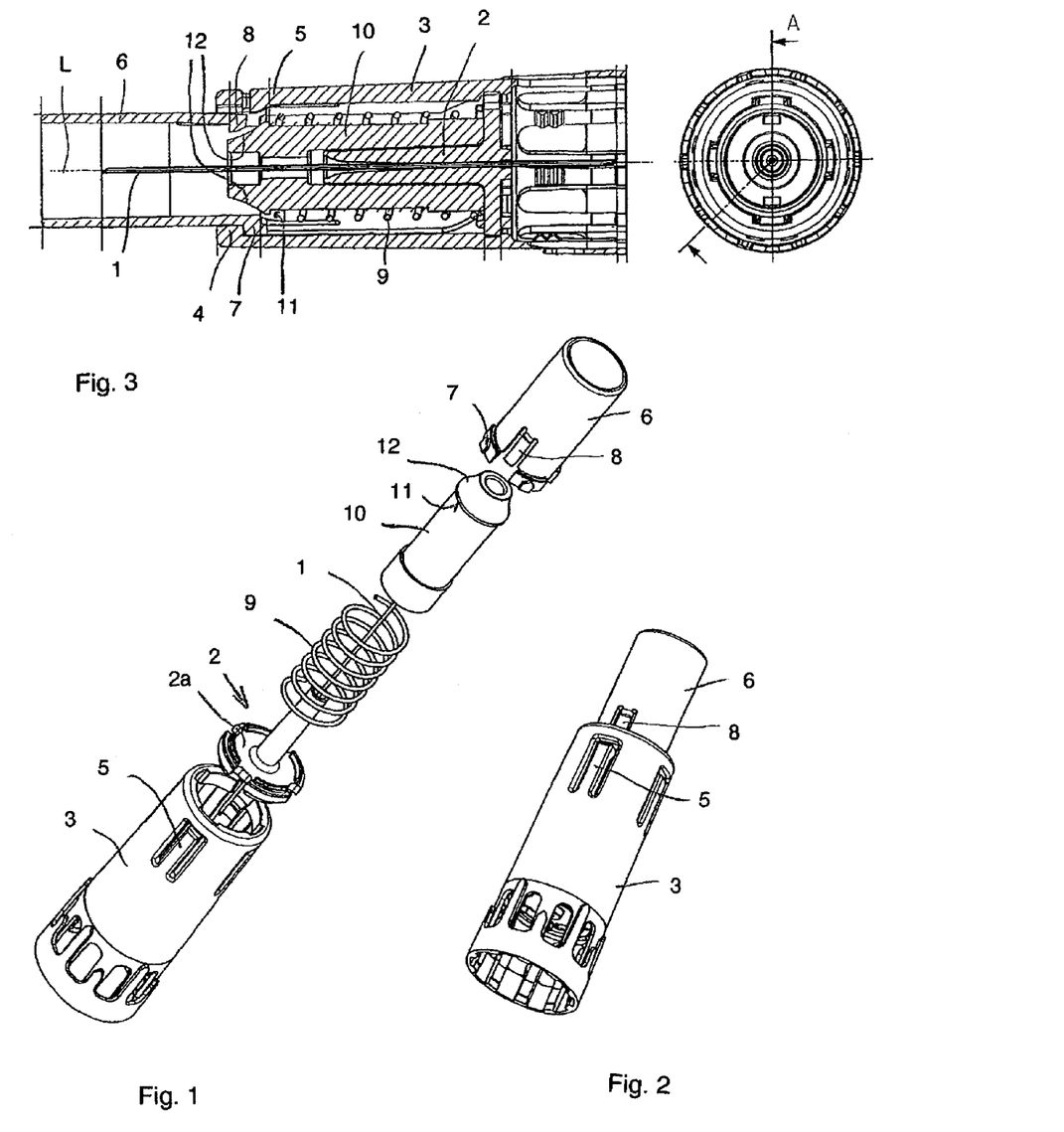
FIG. 1 illustrates an exemplary embodiment of a needle guard device in accordance with the present invention.
FIG. 2 is a perspective view of the needle guard device of FIG. 1 in the assembled state.
FIG. 3 illustrates the needle guard device of FIG. 1 in an initial state.

FIGS. 1 and 2 provide a perspective diagram illustrating a needle guard device which can be fitted on a distal end of an injection device. The injection device may be of the type which enables a dose of an injectable product, for example insulin, to be set or selected, and the set dose to be dispensed on a repeated basis. It is also may be of the type that enables the dose to be re-set with each injection. The injection device may be an injection pen, of the type commonly used for self-administering medicaments, for example for the treatment of diabetes. The injection device is therefore designed for administering several injections for a longer service life. In some embodiments of the present invention, the needle guard device which surrounds an injection needle 1 for the injection device, on the other hand, is designed for a single injection only, i.e. for one-off use only. In readiness for use, it is attached to the distal end of the injection device, for example screwed onto it or, as in the case of the embodiments described as an example, push-fitted on it, and removed and disposed of after the injection.

As mentioned above, the needle guard device comprises the injection needle 1, a needle holder 2 and two sleeve-shaped structures, namely an outer sleeve 3 and an inner sleeve 6, which form a needle guard telescope. The inner sleeve 6 is able to move axially relative to the outer sleeve 3 and relative to the injection needle 1. FIG. 2 illustrates the needle guard device in an initial state in which the inner sleeve 6 assumes a distal (front or forward) position relative to the outer sleeve 3, in which it covers the injection needle 1 to beyond its needle tip and thus forms a view-blocking guard or cover. The inner sleeve 6 may, therefore, be thought of and/or referred to as needle guard 6. The outer sleeve 3 serves to lock the needle guard 6 after the injection and may, therefore, be thought of and/or referred to as lock mechanism 3.

FIG. 3 also illustrates the needle guard in the initial state. In addition to the longitudinal section, a cross-section is also illustrated. The position of the longitudinal section A-A is indicated in the diagram illustrating the cross-section.

The lock mechanism 3 has a proximal fixing portion for attaching the needle guard device to an injection device. The needle holder 2 is inserted in the sleeve-shaped lock mechanism 3 and in the inserted state is connected to the lock mechanism 3 so that it is not able to move axially or in rotation about the longitudinal axis L. As far as the function of the lock mechanism 3 is concerned, namely protecting user or handlers from accidental sticks by the injection needle 1, the lock mechanism 3 could be integrally molded with the needle holder 2. When it comes to assembling the needle guard device, however, it is of advantage to manufacture it separately from the needle holder 2. The needle holder 2 has a base 2a, from the central region of which a retaining portion for the injection needle 1 projects in the distal direction. The longitudinal axis L of the injection needle 1 coincides with the proximal-distal axis. If, as in some preferred embodiment, the product or substance to be injected is conveyed by a reciprocating plunger, the axial direction advantageously coincides with the forward-drive direction of the plunger. The injection needle 1 is axially secured to the needle holder 2 in the retaining portion. The injection needle 1 extends through the retaining portion of the needle holder 2. It extends in the proximal direction into a chamber of the fixing portion surrounded by the wall but sits behind a proximal edge of the wall. This chamber is sealed to render it sterile by a film, which is secured to the wall of the needle holder 2 at the proximal end. When the needle guard device is attached to the injection device, the film is destroyed and the proximal pointed end of the injection needle pierces a membrane sealing a distal end of a container filled with the product. As a result, during the process of attaching it to the injection device, a flow connection is simultaneously established between the injection needle 1 and the product container.

Toward its distal (the front, forward or injection end) end, the injection needle 1 has an injection portion incorporating the needle tip. The length of the injection needle is dimensioned for a subcutaneous injection. Accordingly, the injection portion penetrates the skin and through the skin as far as a subcutaneous injection point. The injection portion extends in the proximal direction from the free needle tip as far as the axial level of the distal end of the lock mechanism 3. In the initial state, the needle guard 6 assumes its distal-most position, which is predefined by the co-operation of a stop 4 of the lock mechanism 3 with a complementary stop 7 of the needle guard 6. The stop 4 is formed by a shoulder projecting radially inward from the lock mechanism 3 and the complementary stop 7 is formed by a shoulder projecting radially outward from the needle guard 6.

The needle guard device also has a return element 9, which is a mechanical compression spring in the embodiment illustrated as an example. The return element 9 exerts an elastic force acting on the needle guard 6 in the distal direction, by means of which it pushes the complementary stop 7 against the stop 4. The return element 9 is axially supported on the lock mechanism 6 and the needle holder 2.

The needle guard device also has a locking member 10 for the needle guard 6. The locking member 10 extends the retaining portion of the needle holder 2 in the distal direction. It has a cylindrical and, in the embodiment illustrated as an example, circular cylindrical external face, which lies opposite and faces a cylindrical and, in the embodiment illustrated as an example, circular internal face of the lock mechanism 3 disposed parallel at a distance apart. The external face of the locking member 10 and the internal face of the lock mechanism 3 radially bound an axially extending annular gap into which the needle guard 6 is able to move. The return element 9 is also disposed in the annular space. The internal and external surfaces mutually bounding the annular space guide the needle guard 6 during its movement in a sliding contact and also guide the return element 9 as it springs in and out in the exemplary embodiment.

The external face of the locking member 10 forms a guide 12 for the needle guard 6, which is a slide guide in the exemplary embodiment. The guide 12 forms a distal end portion of the locking member 10. The guide 12 is a smooth surface extending circumferentially about the longitudinal axis L. It extends from the distal end of the locking member 10 in the proximal (rearward) direction and has a radially outward inclination. The locking member 10 becomes thicker at its external surface, namely from the distal end in the proximal direction, and falls abruptly away at a proximal end of the thicker region or wider region in a shoulder extending circumferentially about the longitudinal axis L except for an outer circular cylindrical portion of the locking member 10. Adjoining this portion, which is longer than the guide 12, at the proximal end of the locking member 10 is a thicker end portion. The transition between the middle portion and the proximal end portion is also abrupt, in the form of a shoulder. The guide 12 curves continuously from its distal end to its proximal end, the shoulder 11. In the exemplary embodiment, the inclination of the guide 12 becomes continuously more pronounced from its distal end in the proximal direction to close to the shoulder. The guide 12 may alternatively have a constant inclination or a gradually reducing inclination in the proximal direction.

The needle guard 6 has two locating elements 8, each of which co-operates with the guide 12. In the section illustrated in FIG. 3, only one of the locating elements 8 is visible. The other locating element 8 is of the same shape as the one illustrated and also the same in terms of the way it co-operates with the guide 12. The locating element 8 is provided in the form of a flexibly elastic lug extending out in the proximal direction from a root region in the casing of the needle guard 6 and has a shoulder projecting radially inward at its proximal end. The shoulder results in an inwardly projecting cam on the proximal end of the locating element 8. This cam sits in a sliding contact with the guide 12. When the needle guard 6 moves in the proximal direction, the cam slides on the guide 12 so that the locating element 8 is gradually bent elastically outward to an increasing degree, due to the inclined contour of the guide 12. The shoulder at the proximal end of the guide 12 constitutes a complementary locating element 11 for each of the locating elements 8.

The locking member 10 is connected to the needle holder 2 sufficiently securely to prevent it from leaving the position illustrated in FIG. 2 due to accelerations, for example if subjected to vibrations or impact, such as will normally occur during transportation or handling. However, the connection is releasable. The connection is established by a frictional contact between the needle holder 2, namely its retaining portion, and the locking member 10. The seating surfaces co-operating in this frictional contact taper in a conical arrangement in the distal direction.

When the frictional contact connection is released, the locking member 10 slides in the distal direction relative to the injection needle 1. The injection needle 1 extends through the locking member 10, which has a central bore for this purpose.

The locking member 10, generally or as a whole, has the shape of a slim bolt. It imparts stiffness to the needle guard 6 and to its locating elements 8 with respect to the radial direction.

One function of the lock mechanism 3 is to establish a locking connection with the needle guard 6 to prevent it from moving in the proximal direction when it is disposed in a distal guard position. In the guard position, the needle guard 6 assumes the same position by reference to the axis L as it does in the initial position illustrated in FIG. 3. However, when the needle guard 6 is in the guard position, it is prevented from moving in the proximal direction by the lock mechanism 3. To enable it to fulfil the locking function, the lock mechanism 3 has two locking elements 5. The locking elements 5 are respectively provided in the form of a flexibly elastic lug. The locking elements 5 are disposed in the sleeve casing of the lock mechanism 3, each extending out in the distal direction from a proximal base or root region. The locking elements 5 each have a free distal end. The distal end faces of the locking elements 5 acts as stop surfaces for the proximal end faces of the locating elements 8 lying axially opposite when the needle guard 6 is in the guard position. The locking elements 5 therefore respectively act as a lock stop and the locating elements 8 respectively act as a complementary lock stop to lock the needle guard 6 in the guard position. In the guard position, the needle guard surrounds the injection portion of the injection needle 1 to beyond its needle tip.

In the initial state illustrated in FIG. 3, the lock stop of the locking element 5 and the lock complementary stop of the locating element 8 are not engaged. The locating element 8 extends in the proximal direction, terminating just short of the guide 12 or sits at least free of tension on the distal end of the guide 12. From this position, it can be moved radially inward past the locking element 5 unhindered as the needle guard 6 is moved in. The same applies to the pair comprising the locking element 5 and locating element 8 offset by 180° in the circumferential direction. Although, in some preferred embodiments, the needle guard device has several pairs of co-operating elements 5 and 8 and these are advantageously disposed in a symmetrical arrangement about the axis L, a single pair of elements 5, 8 is enough to establish the lock.

A description will be given below with reference to FIGS. 4 to 7 to explain the sequence which takes place during an injection.

Once the user has attached the needle guard device to the injection device as described above, the injection needle 1 is primed. The user then selects the dose to be injected. Having selected the dose, he places the injection device on the desired injection point of the skin via the distal end face of the needle guard 6 and pushes the injection device against the skin. Due to this pressing action in the distal direction, the needle guard 6 moves axially against the elastic force of the return element 9 through the annular gap between the lock mechanism 3 and the locking member 10. The needle guard 6 is axially guided relative to the lock mechanism 3 but is not able to rotate. In what is the first distal portion of the movement, the locating elements 8 slide along the guide 12. The guide 12 and locking elements are shaped and spaced radially apart from one another so that the locating elements 8 are able to move radially inward past the respective co-operating lock element 5 without any difficulty. The lock mechanism 3 becomes inwardly wider in the circumferential region of its locking elements 5 in the proximal direction to the degree that the locating elements 8 are able to bend outward virtually unhindered between the guide and the locking elements 5, and in the ideal situation without the locking elements 5 deforming. At the proximal ends of the guide 12, the locating elements 8 move across the edges distally bounding the complementary locating elements 11 at this point and inward due to their natural rebounding elastic force; they therefore snap into the complementary locating elements 11. The locating elements 8 and complementary locating elements 11 are now hooked to one another in pairs in a driving connection.

As explained above, the internal face of the locking elements 5 facing the guide 12 is shaped so that a sufficiently large distance is left free between the internal face and the guide 12 across the entire stroke of the needle guard 6 so that the locating element 8 does not exert any pressure on the locking element 5 or at least any outwardly directed pressure on the locking element 5. The complementary locating element 11 and the guide 12 are also shaped so that in the initial position, the locating element 8 is bent outward from its distal initial position in the driving connection and is therefore at a greater distance from the central longitudinal axis L in the driving connection than in the distal initial position. In the driving connection, an external face of the locating element 8 facing the locking element 5 is at a greater distance from the central longitudinal axis L than the locking element 5 on its internal face in the distal region.

Figure 4:
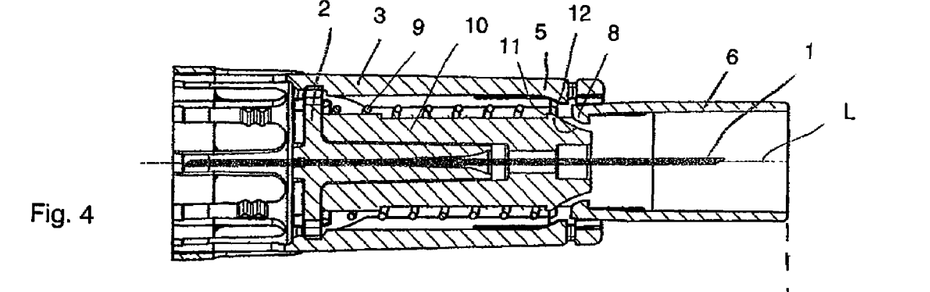
FIG. 4 is a longitudinal section different from that of FIG. 3, illustrating the needle guard device in the initial state.

FIG. 4 illustrates the needle guard device in an initial state prior to use, in which the needle guard 6 assumes the distal initial position. In the initial position, the needle guard 6 is held on the lock mechanism 3 by the co-operating stops 4 and 7 (FIG. 3). The two locating elements 8 lie distally immediately in front of the guide 12 and are relaxed. When an axial pressure is applied to the needle guard 6 in the proximal direction, the needle guard 6 moves in the proximal direction relative to the lock mechanism 3 and to the locking member 10 disposed in its proximal initial position. Coinciding with the start of the movement, after an initial or triggering stroke Y, the locating elements 8 move into a guiding contact with the guide 12 and bend radially outward, conforming to the inclination of the guide 12. The locating elements 8 move along the guide 12 in the gap between the locking member 10 and lock elements 5, and are bent radially outward to a constantly more pronounced degree until reaching the proximal end of the guide 12, and the locating elements 8 snap radially inward behind the complementary locating element 11 due to their elastic rebounding force, thereby establishing the driving connection. From the intermediate or triggering position Y, the needle guard is no longer able to move back into the unlocked initial position when relieved of the external pressing force and is thus left to its own devices.

Figure 5:
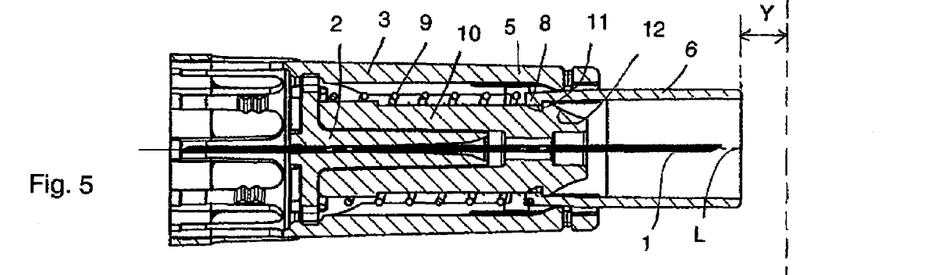
FIG. 5 illustrates the needle guard device in a triggering position.

FIG. 5 illustrates the needle guard device with the needle guard 6 in the triggering position Y. Due to the position of the complementary locating element 11, pushed far forward in the distal direction, the driving connection was already established before the tip of the injection needle 1 was projecting in the distal direction beyond the needle guard 6. In the embodiment illustrated as an example, the needle tip is or rests back from the needle guard 6 by a short distance. Further pressure applied to the needle guard 6 causes the needle guard 6 to move farther into the lock mechanism 3 against the force of the spring element 9. During this additional retracting movement, the locating elements 8 move across the axially straight, cylindrical, circumferential surface adjoining the complementary locating element 11 in the proximal direction.

Figure 6:
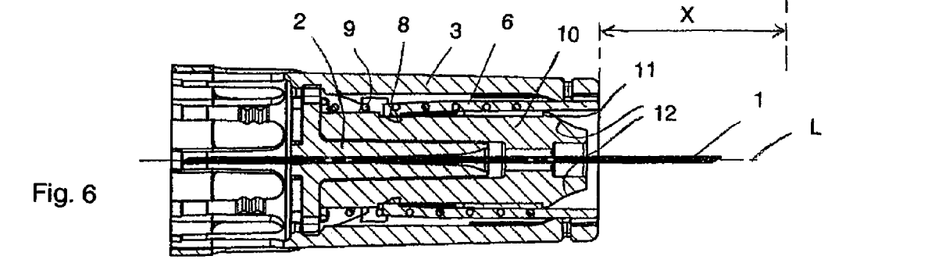
FIG. 6 shows the needle guard device in the releasing position.

FIG. 6 illustrates the needle guard device after effecting the releasing stroke X with the needle guard 6 in the releasing position. The needle guard 6 has moved into the axial overlap with the lock mechanism 3 by its whole length. In this fully retracted state, the distal end faces of the lock mechanism 3, needle guard 6 and locking member 10 are on the same axial level. The injection needle 1 extends beyond the common end face by its full injection portion, i.e. the injection needle 1 has penetrated the skin and the subcutaneous tissue lying underneath as far as the desired penetration depth as measured along the injection needle 1, and the set dose can be administered. During administering, only the pressure needed to overcome the rebounding elastic force of the spring element 9 need be applied. Once the set dose has been administered, the user moves the injection device axially away from the injection point in the proximal direction so that the needle guard 6 is relieved of external pressure.

When the needle guard 6 is relieved of the external force, the needle guard 6 automatically moves forward in the distal direction again due to the rebounding force of the spring element 9 until the locating elements 8 move into an abutting contact with the complementary locating element 11. The distance at which the complementary locating element 11 is from the contact surface of the needle holder 2 in the initial position (FIG. 4) is dimensioned so that the locking member 10, now in the re-established driving connection produced by the locating elements 8 and the complementary locating element 11, is driven in the distal direction by the needle guard 6. The same happens when the needle guard 6 is relieved of the external force in the triggering position Y. During the course of the joint movement of the needle guard 6 and locking member 10, the locating elements 8 move in the distal direction in front of the locking elements 5 of the lock mechanism 3. The locating elements 8, i.e. the ends thereof which have located, are radially farther out than is the case when the needle guard 6 is in the initial position. During the outward movement, the locking elements 5 are therefore bent radially outward and snap back radially inward as soon as the locating elements 8 have passed them due to their natural elastic rebounding force.

Figure 7:
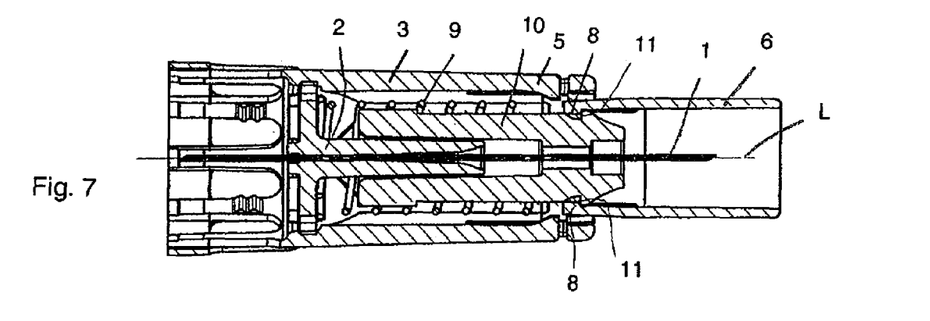
FIG. 7 shows the needle guard device in the guard position.

FIG. 7 illustrates the needle guard device after the injection, with the needle guard 6 in the distal-most position. At the end of the movement of the needle guard 6 in the distal direction, the needle guard device automatically locks via or through the co-operating locating elements 8 and locking elements 5 so that the distal-most position is now the locked guard position of the needle guard 6.

The locking member 10 supports the locating elements 8 radially inwardly so that they can not be moved out of the lock connection with the locking elements 5. The locking elements 5, locating elements 8 and guide 12 are advantageously shaped so that the locking elements 5 are elastically biased in the distal direction to a relevant degree only during the movement of the needle guard 6. The locating elements 8 which bend outward during the retracting movement should at most cause the locking elements 5 to bend to a significantly lesser degree. In some preferred embodiments, the locking elements 5 are not biased at all during the retracting movement. In the embodiment illustrated as an example, this is achieved due to the inclined contour of the internal faces of the locking elements 5 and guide 12 as viewed in longitudinal section and the slim locating elements 8.

The complementary locating elements 11 are disposed with respect to the axial direction so that they are axially overlapped by the lock mechanism 3 when the needle guard 6 (which also may be thought of and/or referred to as a cover) is in the guard position, so that the lock mechanism 3 prevents manipulations of the locating elements 8 which could cause the locating elements 8 to move out of the driving connection.

After the injection, the user removes the needle guard device from the injection device and disposes of it. For a new injection, a new needle guard device in the initial state illustrated in FIGS. 3 and 4 is attached to the injection device.

Figure 8:
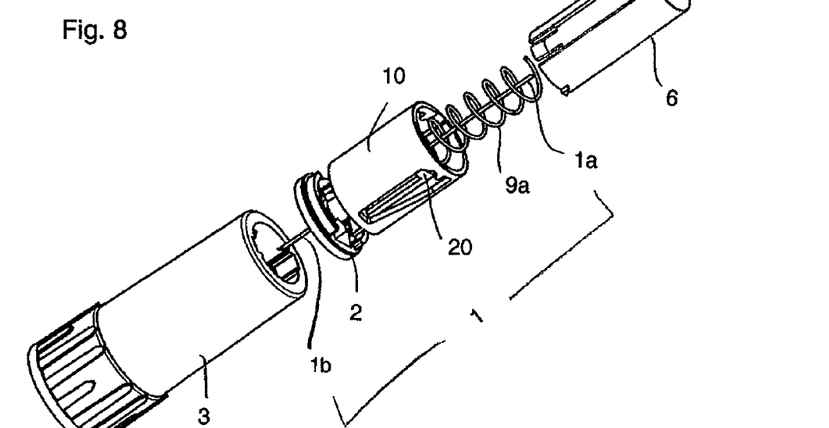
FIG. 8 illustrates another exemplary embodiment of a needle guard in accordance with the present invention.

FIG. 8 illustrates a needle guard device based on a second embodiment in accordance with the present invention, with its components aligned along a central longitudinal axis L one after the other in the order in which they are assembled. The needle guard device comprises an injection needle 1, which is held by a needle holder 2, as was the case in the first embodiment, a lock mechanism 3 which also has a fixing and guide mechanism for attaching the needle guard device to the distal end of an injection device and forms a non-rotatable, axial guide of the needle guard 6, a spring element 9a and a locking member 10. The needle guard device also has a distal needle guard 6.

The needle holder 2 is inserted in the sleeve-shaped lock mechanism 3 and secured so that it is not able to move. A needle injection portion 1a projects beyond the lock mechanism 3 in the distal direction by a length suitable for administering a subcutaneous injection. In the proximal region, the lock mechanism 3 surrounds a needle connecting portion 1b and projects beyond it in the proximal direction. The needle guard 6 is retained in the initial position relative to the lock mechanism 3 against the force of the spring element 9a by means of the locking member 10.

Figure 9:
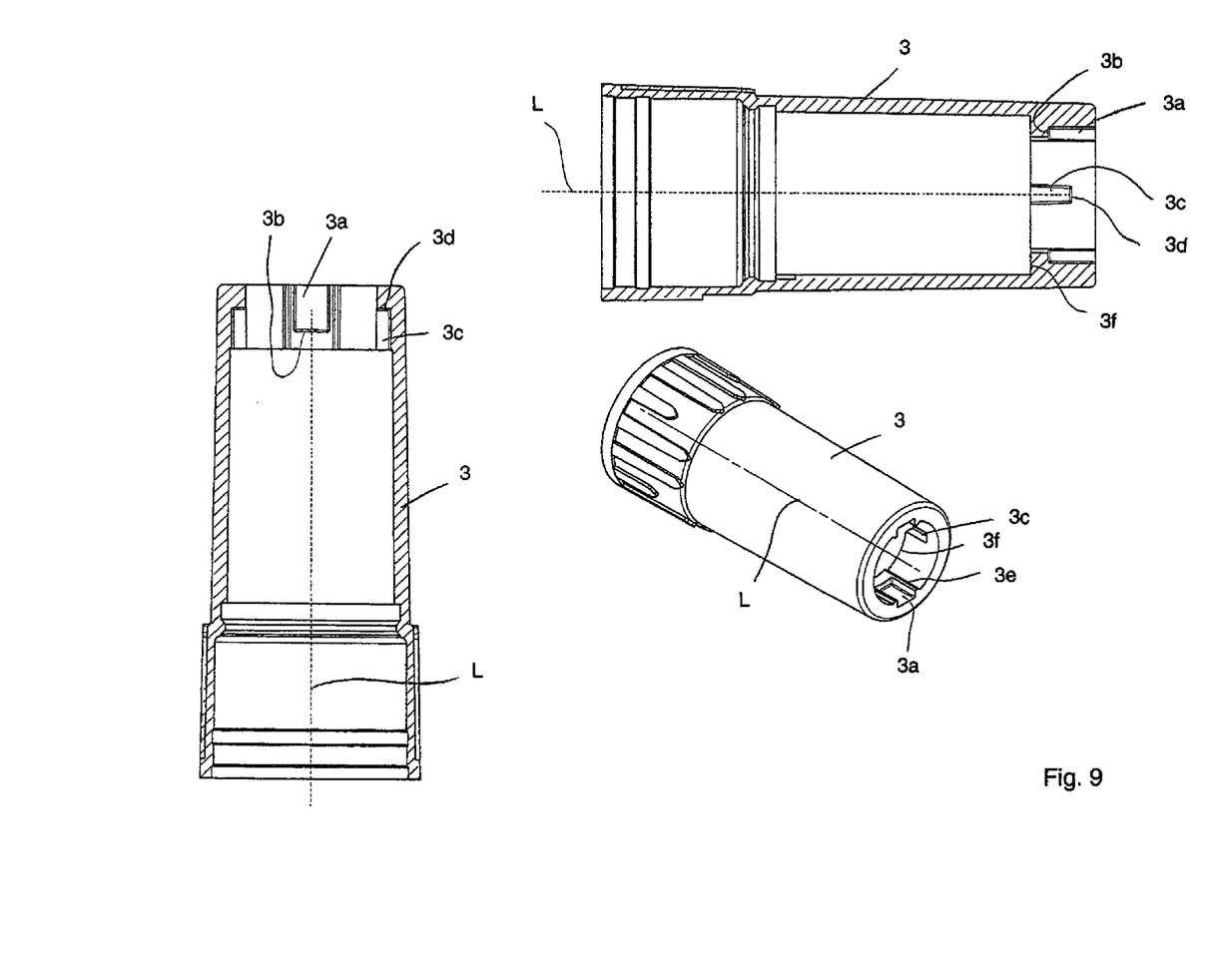
FIG. 9 illustrates a lock mechanism associated with the embodiment of FIG. 8.

FIG. 9 shows the lock mechanism 3 in two longitudinal sections, offset from one another by 90°, and a perspective view. The lock mechanism 3 has two pocket-shaped recesses 3a in the internal face at the distal end extending circumferentially about the longitudinal axis L. The recesses 3a merge into the internal surface via a steep shoulder at their proximal end in each case. The two shoulders each form a translation stop 3b pointing in the distal direction. Disposed to the side of the recesses 3a are respective axially extending guides 3e to ensure that the needle guard 6 is guided in a straight line. Two other pocket-shaped recesses 3c are provided at the distal end of the lock mechanism 3 in the same internal face, which are offset from the recesses 3a on the circumference of the internal face by 90° in each case. The recesses 3c each merge into the casing internal face via a steep shoulder at their distal end. The two shoulders each form a translation stop 3d pointing in the proximal direction. Also still in the distal end portion, the lock mechanism 3 acts as a translation stop 3f for the locking member 10. The translation stops 3b and 3d define the guard position of the needle guard 6. The translation stop 3d establishes a lock to prevent extraction again and the translation stop 3b establishes a lock to prevent retraction and thus replaces the lock stop of the locking element 5 in the first embodiment.

Figure 10:
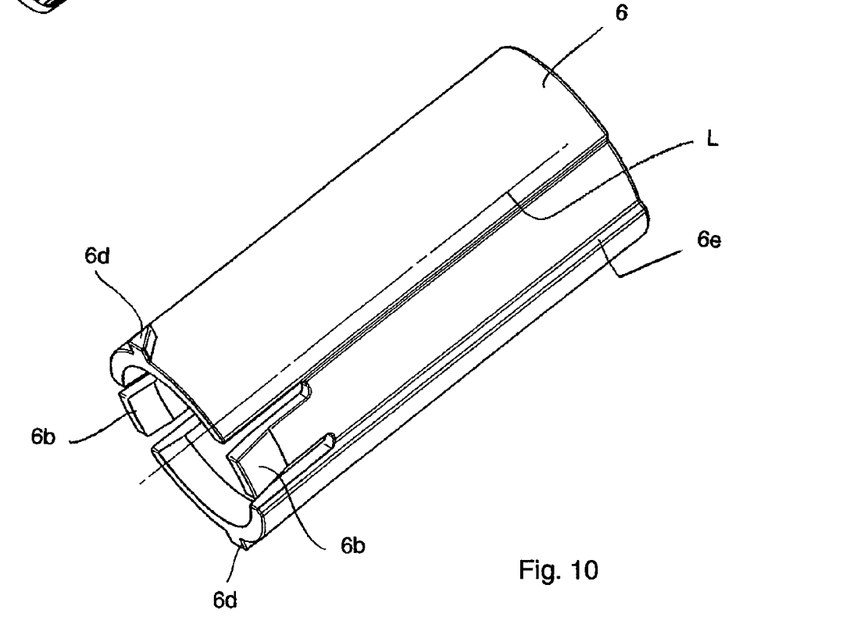
FIG. 10 illustrates a distal needle guard of the embodiment of FIG. 8.

FIG. 10 shows the needle guard 6. The needle guard 6 has axial guides 6e, which co-operate with the guides 3e of the lock mechanism 3 and with them guide the needle guard 6 linearly but prevent it from rotating. Disposed at its proximal end, the needle guard 6 has two locking elements 6b offset from one another in the circumferential direction by 180°, which are provided in the form of resilient lugs in this exemplary embodiment. The locking elements 6b are outwardly inclined in the proximal direction. Finally, two locating elements 6d in the form of outwardly projecting cams are provided on the external circumference of the needle guard 6, likewise at its proximal end offset from one another by 180° in the circumferential direction. On a face pointing in the circumferential direction about the longitudinal axis L, the locating elements 6d respectively have an inclination with respect to the longitudinal axis L so that the respective locating element 6d forms a ramp on the relevant side.

Figure 11:
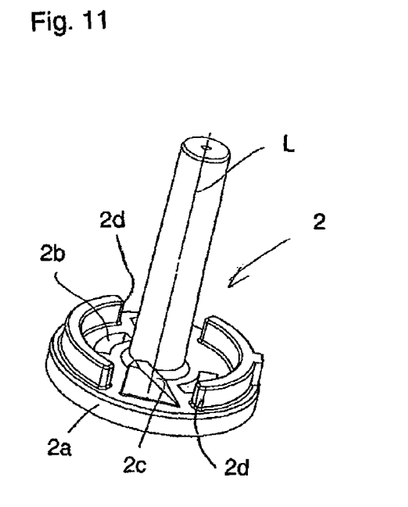
FIG. 11 is a perspective diagram illustrating a needle holder of the embodiment of FIG. 8.
Figure 12:
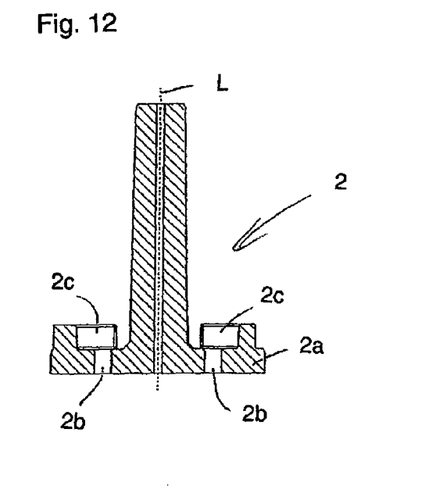
FIG. 12 shows the needle holder in longitudinal section.

FIGS. 11 and 12 illustrate the needle holder 2 of the second embodiment. The needle holder 2 has a base 2a and a central retaining region for the injection needle 1 extending out from the base 2a. The base 2a is provided with two passages 2b, through which the needle guard 21 is able to retract in the proximal direction into a proximal guard position and which also serve as a means of locking the needle guard 21 in its guard position. Projecting out from the base 2a in the distal direction outside of and adjacent to the retaining region are two projections offset from one another in the circumferential direction about the longitudinal axis by 180°, each of which is inclined in a ramp shape on a distal side to form a respective inclined guide 2c for the locking member 10. Facing the ramp-shaped, inclined guides 2c, another respective projection 2d extends out from the base 2a in the distal direction. The plane of the section illustrated in FIG. 12 extends through the longitudinal axis L and the gaps between one of the respective projections forming the guides 2c and the projection 2d facing the respective guide 2c.

Figure 13:
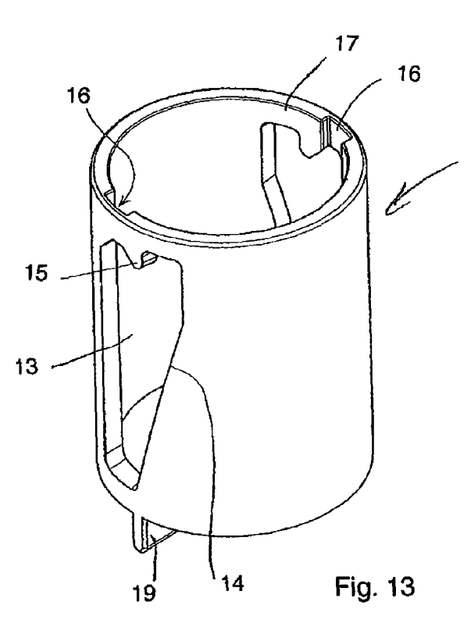
FIG. 13 is a perspective diagram illustrating a locking member of the embodiment of FIG. 8.
Figure 14:
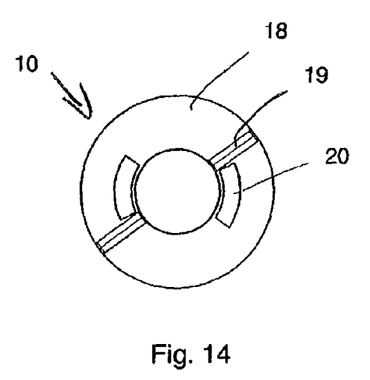
FIG. 14 is a plan view of the locking member in the distal direction.

FIG. 13 is a perspective view of the locking member 10. FIG. 14 is a plan view of the bottom face of the locking member 10, i.e. a view in the distal direction. The locking member 10 is hollow cylindrical. Molded into the casing of the locking member 10 are two cut-outs 13 offset from one another in the circumferential direction by 180° which extend through the casing and respectively form a track 14 inclined in the circumferential direction on one side. A projection 15 extends out in the proximal direction from a distal peripheral strip of the locking member 10 into the respective cut-out 13. The two cut-outs 13 are circumferentially framed by the casing of the locking member 10 and an axially extending passage 16 is respectively formed distally in front of the tracks 14 in the internal face of the casing next to the projections 15, which extends continuously from the distal end of the locking member 10 to the respective cut-out 13. When the needle guard device is assembled, the locking member 10 with its two passages 16 moves across the locating elements 6d of the needle guard 6 so that the locating elements 6d move into the respective co-operating cut-out 13. The locating elements 6d are then moved behind the respective projection 15 into the circumferential region 17 by rotating the locking member 10, still during the assembly process, so that the locating elements 6d locate behind the distal edge of the locking member 10 in its circumferential regions 17. The two circumferential regions 17 respectively form a translation stop and in this sense a complementary locating element 17 for the respective co-operating locating element 6d. The needle guard 6 is retained on the lock mechanism 3 in this abutting contact against the force of the spring elements 9 and 9a. The projections 15 are disposed in the direction extending transversely to the longitudinal direction of the injection needle 1 between the passage 16 and the complementary locating element 17. In a guide contact with the locating elements 6d, they separate the passage 16 from the respective co-operating complementary locating element 17 so that the locating elements 6d either overlap the complementary locating elements 17 when the locking member 10 is in a first position or overlap the passages 16 when the locking member 10 is in a second position. The projections 15 fulfill the function of separating elements.

The locking member 10 is able to move axially backwards and forwards relative to the needle holder 2 and lock mechanism 3 and also rotate about the longitudinal axis L.

On its bottom face, the locking member 10 has an annular base 18 extending radially inwardly at the proximal end of its casing and locating elements 19 projecting out from the base 18 in the proximal direction, in total two locating elements 19, which are offset from one another in the circumferential direction by 180°. Two passages 20 are provided in the base 18 for the proximal guard 21, offset from one another by 180° in the circumferential direction.

Figure 15:
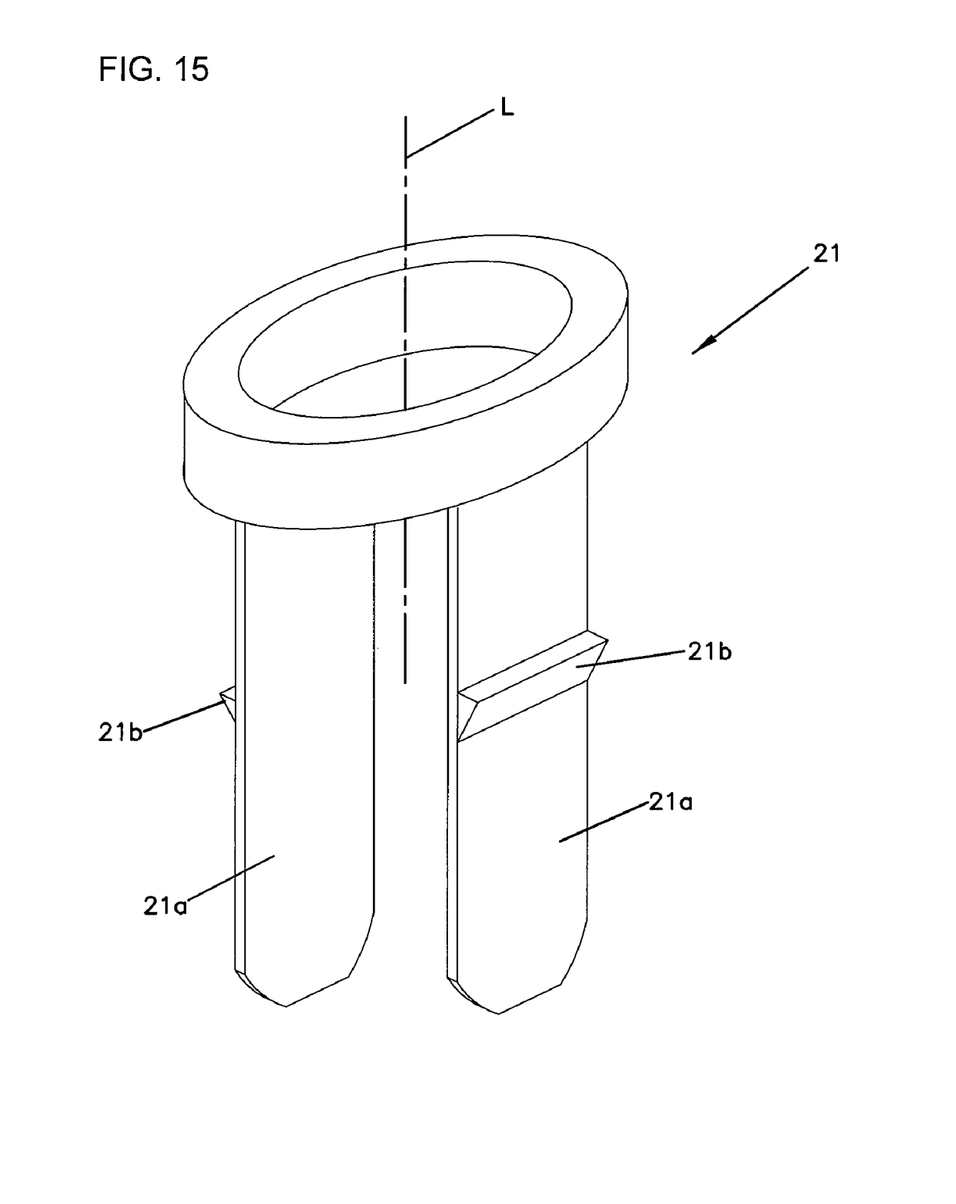
FIG. 15 shows a proximal needle guard of the embodiment of FIG. 8.

FIG. 15 illustrates the proximal needle guard 21. The needle guard 21 has an annular base at a distal end and flexible legs or fingers 21a extending elastically out from the base in the proximal direction toward the direction of the longitudinal axis L. A projection 21b is provided on the external face of the fingers 21a in each case. The projections 21b taper in an arrow shape in the proximal direction and each forms a stop for the needle guard 21 pointing in the distal direction.

Figure 16:
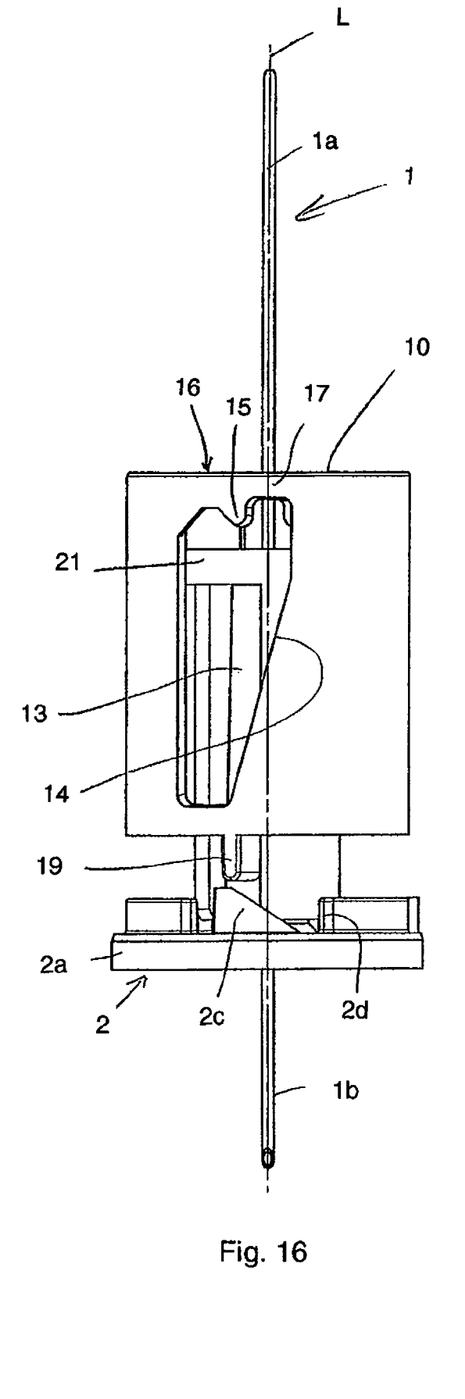
FIG. 16 illustrates a sequence control associated with the embodiment of FIG. 8 in an initial state prior to an injection.
Figure 18:
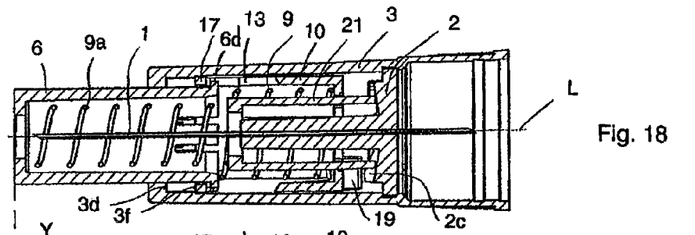
FIG. 18 illustrates the needle guard device of FIG. 8 in the initial state.

FIG. 16 illustrates the components which co-operate to lock the needle guard 21, the needle guard 21 having assumed a distal initial position which simultaneously also corresponds to a releasing position of the needle guard 21. In the initial position, the needle guard 21 sits completely behind the connecting portion 1b of the injection needle 1 in the distal direction. It also sits back behind the base 2a of the needle holder 2, i.e. the spring element 9a pushes the needle guard 21 in the proximal direction against the base 2a in its initial position. The fingers 21a extend through the passages 20 of the locking member 10 (FIG. 14). When the needle guard device is in the initial state, the passages 20 and the passages 2b of the needle holder 2 are offset from one another in the circumferential direction. The locating elements 19 of the locking member 10 are disposed axially facing the guides 2b of the needle holder 2. The spring element 9a holds the locking member 10 via the needle guard 6 in the distal initial position illustrated in FIG. 16 in which the needle guard 6 locates behind the locking member 10 in the circumferential regions 17 by means of its locating elements 6d, pulling it into the distal initial position. This initial position is also illustrated in FIG. 18.

The needle holder 2 and the locking member 10 also act as a sequence controller for locking the needle guard 6 to lock it in the guard position when it has moved out of its initial position into at least the triggering position and is then relieved of the external force causing the movement in the proximal direction.

Figure 17:
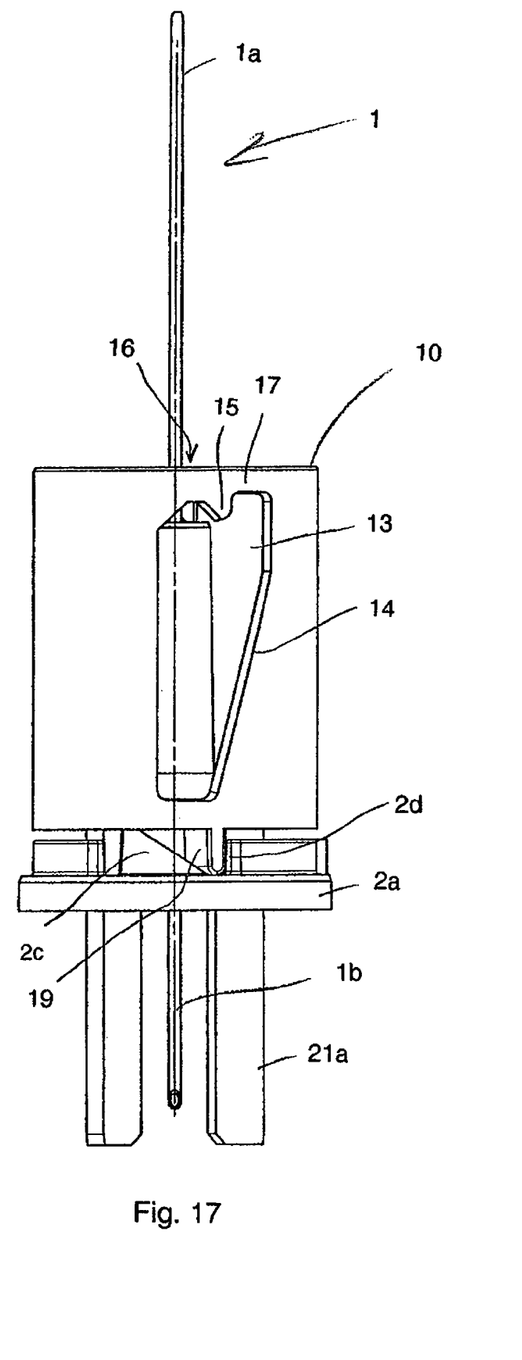
FIG. 17 illustrates the sequence control in an end state after an injection.
Figure 22:
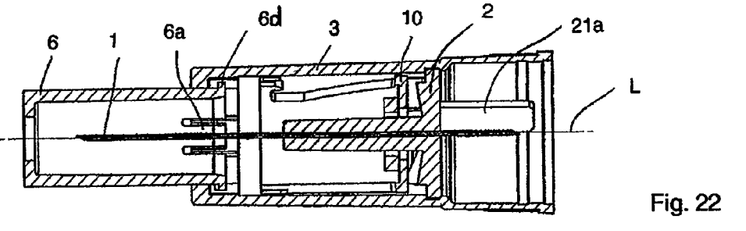
FIG. 22 illustrates the needle guard device with the needle guard in the guard position.

FIG. 17 illustrated the needle guard device and the needle guard 21 disposed in its proximal guard position. FIG. 22 illustrates the needle guard device as a whole, likewise in this end state.

A description will be given below explaining how the needle guard device based on the second exemplary embodiment operates with reference to FIGS. 18 to 22 but also with reference to FIGS. 8 to 17, including FIGS. 16 and 17.

The needle guard device is connected to the injection device in the initial state illustrated in FIG. 18, for example screwed to it or clipped onto it. As this happens, the needle connecting portion 1b pierces the sealing membrane of the medicament reservoir. A movement of the needle guard 21 does not yet take place during the fitting process.

Figure 21:
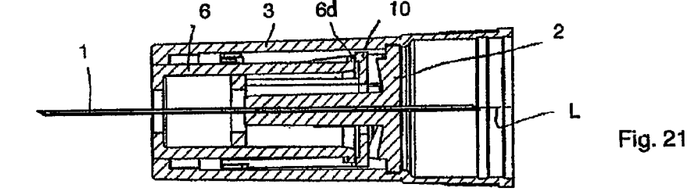
FIG. 21 illustrates the needle guard device with the needle guard in the releasing position.

The user then pierces the skin through to the subcutaneous tissue at the desired injection point with the injection needle 1. As this happens, the needle guard 6 moves in the proximal direction relative to the needle holder 2 so that, conversely, the needle injection portion 1a projects forward. FIG. 21 illustrates the needle guard device in the piercing state whilst the medicament is being administered.

Figure 19:
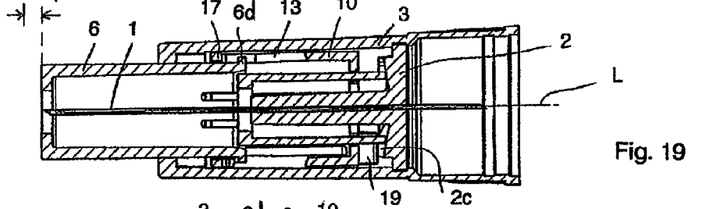
FIG. 19 illustrates the needle guard device at the start of a triggering phase.
Figure 20:
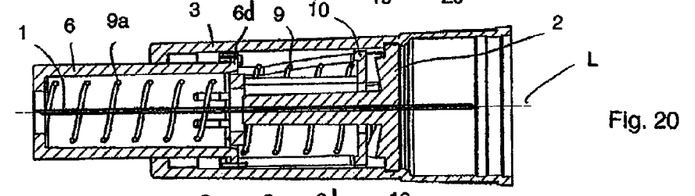
FIG. 20 illustrates the needle guard device at the end of the triggering phase.

Due to the external force acting on the needle guard 6 in the proximal direction, the needle guard 6 moves in the proximal direction against the rebounding spring force of the spring element 9a relative to the needle holder 2 and also relative to the locking member 10. Another spring element 9 surrounding the needle guard 21 is supported on the needle holder 2 in the proximal direction and on the needle guard 6 in the distal direction, namely on its proximal end in the embodiment illustrated as an example. The retracting needle guard 6 therefore pushes on the locking member 10 in the proximal direction via the spring element 9. Since the locating elements 6d are still in a guide contact with the respective co-operating projection 15 at the start of the movement and the needle guard 6 is guided in a straight line and prevented from rotating, the locking member 10 is still not able to rotate. At the end of the triggering stroke, having reached the triggering position Y, the locating elements 6d of the needle guard 6 are moved out of the axial overlap with the projections 15 of the locking member 10. The axial length of the projections 15 simultaneously also defines the length of the triggering stroke Y, i.e. the triggering position Y by reference to the initial position. As soon as the locating elements 6d have passed the proximal end of the respective co-operating projection 15 and the guide contact of the locating elements 6d and the projections 15 has therefore been released, the locating elements 19 are able to slide on the guides 2c. Since the guide contact between the locating elements 19 and the guides 2c has then been established, the locking member 10 rotates relative to the needle holder 2, the lock mechanism 3 and also relative to the needle guard 6 in accordance with the direction of inclination of the guides 2c about the longitudinal axis L, out of the first position illustrated in FIG. 16 into the second position illustrated in FIG. 17, in which the locating elements 6d are in axial alignment with the passages 16. FIGS. 19 and 20 illustrate the locking member 10 at the start and at the end of its rotating movement. Under the effect of the external force, the needle guard 6 moves continuously further against the force of the spring element 9 and also the spring element 9a in the direction toward the releasing position. As this happens, the position of angular rotation of the locking member 10 does not change.

A translating movement is superimposed on the rotating movement, causing the locating elements 19 of the locking member 10 to slide on the respective co-operating guide 2c. The translating and rotating movement is restricted by the abutting contact of the locating elements 19 and the projections 2d. The projections 2d act as stops for the rotating movement. The locking member 10 drives the needle guard 21 with it during the rotating movement because the fingers 21a are extending through the passages 20. As soon as the locking member 10 has reached its neutral position illustrated in FIG. 17, the passages 20 of the locking member 10 (FIG. 14) overlap the passages 2b of the needle holder 2 (FIGS. 11 and 12) so that the fingers 21a of the needle guard 21 are able to pass through the passages 2b due to the force of the spring element 9a. The fingers 21a are pushed by the spring element 9a as far as a point on the distal end of the injection device, for example a distal point of the device itself or the medicament reservoir. Once they have entered the passages 2b of the needle holder 2, the fingers 21a prevent the locking member 10 from being turned back into its initial position (FIG. 16).

When the injection needle 1 has been removed from the tissue and the needle guard 6 has been relieved of pressure as a result, the spring elements 9 and 9a move the needle guard 6 in the distal direction. The position of the two projections 15 in the circumferential direction is selected so that the locating elements 6d move into the passages 16 as the needle guard 6 moves in the distal direction, as a result of which the needle guard 6 is finally released by the locking member 10 and the locking elements 6b are able to move into the recesses 3a of the lock mechanism 3 (FIGS. 9 and 10) and lock the needle guard 6 in its distal guard position due to the lock connection with the lock stops 3b and prevent a movement in the proximal direction. Co-operating with the stops 3d, the locating elements 6d prevent the needle guard 6 from moving completely out of the lock mechanism 3 in the distal direction.

The needle guard device is detached from the injection device with the needle guard 6 locked in its guard position. Under the action of the spring element 9a, the proximal needle guard 21 moves in the proximal direction relative to the needle holder 2 into its guard position illustrated in FIG. 22. In the guard position, the fingers 21a project in the proximal direction beyond the tip of the needle connecting portion 1b. The needle guard 21 is locked by a lock connection between its projections 21b and the base 2a of the needle holder 2, preventing a movement back in the distal direction. The needle guard 21 is supported on the needle holder 2 in the distal direction by its annular base.

Figure 23:
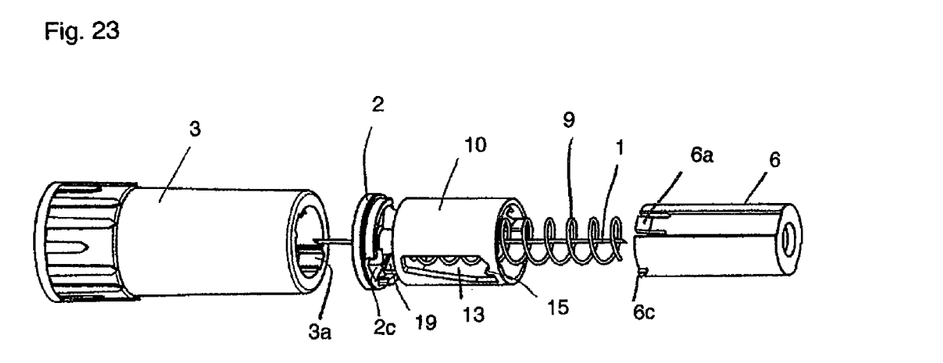
FIG. 23 to 25 illustrate a needle guard device based on another exemplary embodiment in accordance with the present invention.

FIG. 23 illustrates another exemplary embodiment of a needle guard in accordance with the present invention. This embodiment is a modification of the second embodiment described above. The proximal needle guard 21 has been dispensed with. Accordingly, the spring element 9a is also dispensed with. As regards the needle holder 2 and the locking member 10, the passages for the fingers 21a of the needle guard 21 are dispensed with. Otherwise, the third embodiment is the same as the second embodiment and its control sequence proceeds in a similar manner.

Figure 24:
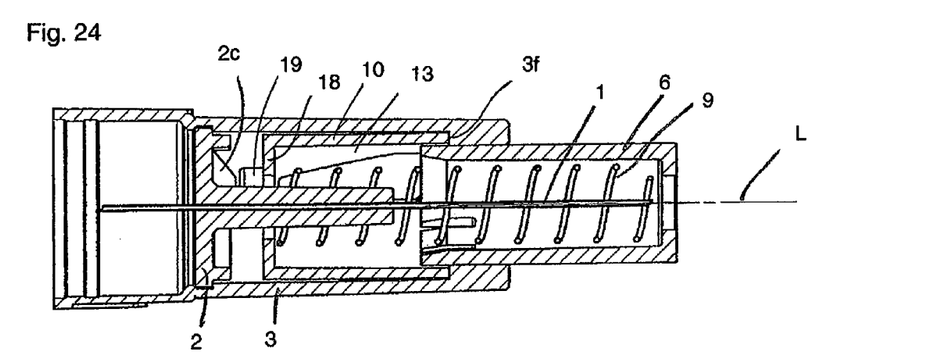
Figure 25:
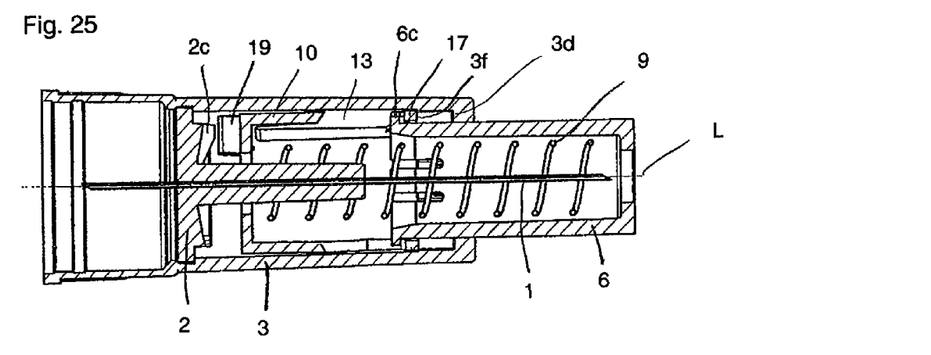

FIGS. 24 and 25 illustrate the needle guard device based on the third embodiment in two longitudinal sections offset from one another by 90°. In FIGS. 24 and 25, the needle guard 6 has assumed its unlocked initial position. The spring element 9 is longer than the spring element 9 of the second embodiment in that it is supported on the base of the locking member 10 in the proximal direction, as is the case with the second embodiment, but in the distal direction is supported on the needle guard 6 close to its distal end. For details of the motion sequence which takes place during an injection, e.g., the components co-operating to produce early triggering of the needle guard 6, reference may be made to the explanation given above in connection with the second embodiment.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A needle guard device for or on an injection device, the needle guard device comprising:
    a) an injection needle extending along a longitudinal axis of the needle guard device,
    b) a needle holder which is attached to or can be attached to the injection device, from which the injection needle extends in a distal direction,
    c) a spring element,
    d) a needle guard element, which can be moved by an external force against a spring force of the spring element from a distal initial position, in which it surrounds the injection needle to beyond a needle tip, in the proximal direction by a releasing stroke as far as a releasing position exposing the injection needle and out of the releasing position in the distal direction as far as a guard position in which it surrounds the injection needle and the needle tip,
    e) a lock mechanism, which locks the needle guard element in a locked connection in the guard position to prevent a movement in the proximal direction, and
    f) a locking member arranged in an interior of the lock mechanism, wherein the locking member is axially movable relative to the lock mechanism upon establishing an engagement with the needle guard element, said engagement established as the needle guard element moves, relative to the lock mechanism and the locking member, into a triggering position disposed between the initial position and the releasing position, wherein
    g) upon reaching the triggering position, the engagement is established by a locating element of the needle guard element moving into a driving connection with a complementary locating element of the locking member, wherein
    h) in the driving connection, the needle guard element slaves the locking member in the distal direction, and due to the spring force returning the needle guard element engaged with the locking member from the triggering position to the guard position, the locked connection is established by the locating element of the needle guard element abutting a lock stop of the lock mechanism, the abutting contact preventing the needle guard element from moving in the proximal direction.

2. The needle guard device as claimed in claim 1, wherein the locking member is able to move relative to at least one of the needle holder and lock mechanism from a first position which the locking member assumes when the needle guard element is in the initial position into a second position, and the locking member prevents the needle guard element from moving out of the guard position in the second position.

3. The needle guard device as claimed in claim 1, wherein a flexibly elastic second lug extending in the longitudinal direction of the injection needle constitutes the locating element and another lug constitutes the lock stop.

4. The needle guard device as claimed in claim 3, wherein the locking member supports the locating element radially inwardly to block a radially inward movement of the locating element in the guard position.

5. The needle guard device as claimed in claim 4, wherein the locking member has a guide for the locating element, which extends in the proximal direction with an inclination radially outward to deflect the locating element radially outwardly during the movement into the triggering position.

6. The needle guard device as claimed in claim 5, wherein the guide is phased out radially inwardly at a proximal end to form the complementary locating element.

7. A needle guard device for or on an injection device, the needle guard device comprising:
   a) an injection needle extending along a longitudinal axis of the needle guard device,
   b) a needle holder which is attached to or can be attached to the injection device, from which the injection needle extends in a distal direction,
   c) a spring element,
   d) a needle guard element, which can be moved by an external force against a spring force of the spring element from the distal initial position, in which it surrounds the injection needle to beyond a needle tip, in the proximal direction by a releasing stroke as far as a releasing position exposing the injection needle and out of the releasing position in the distal direction as far as a guard position in which it surrounds the injection needle and the needle tip,
   e) a lock mechanism, which locks the needle guard element in a locked connection in the guard position to prevent a movement in the proximal direction, and
   f) a locking member arranged in an interior of the lock mechanism, wherein in the distal initial position of the needle guard element, the spring force urges the needle guard element into an abutting engagement with the locking member, and the locking member axially moves relative to the lock mechanism via a force from the spring element when the needle guard element acts in the proximal direction from the distal initial position to a triggering position disposed between the initial position and the releasing position, wherein
   g) the needle guard element moves into the locked connection due to the needle guard element passing through a passage on the locking member to effect a release of the abutting engagement between the needle guard element and the locking member, such that the spring force moves the needle guard element from the triggering position to the guard position.

8. The needle guard device as claimed in claim 7, wherein the needle holder comprises a cam guide with a guide inclined relative to the longitudinal direction of the injection needle and the locking member comprises a locating element which is guided along the guide, and the needle guard element is coupled with the locking member so that it exerts a force on the locking member during the movement into the triggering position, causing the locking member to move into the second position when a guide contact is established between the guide and locating element.

9. The needle guard device as claimed in claim 7, further comprising a locating element of the needle guard element in an abutting contact with a complementary locating element of the locking member in the distal direction, wherein the abutting contact provides the abutting engagement when the needle guard element is in the initial position, wherein the locking member passage extends in the longitudinal direction of the injection needle, and the needle guard element is coupled with the locking member so that the movement of the needle guard element into the triggering position causes a relative movement between the needle guard element and the locking member transverse to the longitudinal axis so that the locating element and the complementary locating element move out of the abutting contact, and the locating element moves into axial alignment with the passage.

10. The needle guard device as claimed in claim 9, wherein the locking member has a separating element extending in the longitudinal direction and disposed between the passage and the complementary locating element, a length of the separating element corresponding to a stroke which the needle guard element effects to reach the triggering position and wherein the separating element is in a guide contact with the locating element as the needle guard element moves into the triggering position, which prevents the relative movement transverse to the longitudinal axis.

11. The needle guard device as claimed in claim 7, wherein the locking member rotates about the injection needle and translates in the longitudinal direction of the injection needle relative to at least one of the needle holder and lock mechanism as the needle guard element moves from the initial position to the triggering position, wherein the rotated locking member aligns the passage with a portion of the needle guard element such that the abutting engagement can be released upon movement of the needle guard element to the guard position.

12. The needle guard device as claimed in claim 11, wherein the needle guard element exerts a force via the spring element on the locking member acting in the proximal direction as it moves into the triggering position.

13. The needle guard device as claimed in claim 11, wherein the injection needle extends from the needle holder in a proximal direction, and the needle guard device further comprises a proximal needle guard and another spring element arranged between the needle guard element and the proximal needle guard, wherein upon moving the locking member rotationally and translationally, the another spring element is tensed and the proximal needle guard aligns with openings formed in the needle holder and the tensed another spring element forces the proximal needle holder in the proximal direction through the openings such that the proximal needle guard shields the injection needle extending in the proximal direction.

14. The needle guard device as claimed in claim 7, further comprising:
   a locating element associated with the needle guard element which engages with a complementary locating element of the locking member when the needle guard element is in the initial position, the engagement preventing a movement of the needle guard element in the distal direction, wherein the needle guard element additionally has a lock element for the locking engagement with the lock mechanism.

15. The needle guard device as claimed in claim 14, wherein the lock mechanism has a complementary lock element for the lock element and at least one of the lock element and complementary lock element is able to move transversely to the longitudinal direction of the injection needle against a spring force to automatically establish a lock connection with the other of the lock element and complementary lock element.

16. The needle guard device as claimed in claim 7, wherein in an initial position of the locking member, the needle guard element is in the distal initial state, and the abutting engagement between the locking member and the needle guard element prevents the needle guard element from movement into the guard position, and upon the needle guard element reaching the triggering position, the needle guard element is released from the engagement with the locking member such that the needle guard element moves in the distal direction past the initial position into the guard position.

17. The needle guard device as claimed in claim 7, wherein the locking member moves relative to at least one of the needle holder and lock mechanism from a first position which the locking member assumes when the needle guard element is in the initial position into a second position, and the locking member prevents the needle guard element from moving into the guard position in the first position.

* * * * *